United States Patent
Brøndum

(10) Patent No.: US 9,750,654 B2
(45) Date of Patent: Sep. 5, 2017

(54) BED

(75) Inventor: Peter Brøndum, Sønderborg (DK)

(73) Assignee: Linak A/S, Nordborg (DK)

( * ) Notice: Subject to any disclaimer, the term of this patent is extended or adjusted under 35 U.S.C. 154(b) by 0 days.

(21) Appl. No.: 13/138,955

(22) PCT Filed: May 3, 2010

(86) PCT No.: PCT/DK2010/000060
§ 371 (c)(1),
(2), (4) Date: Nov. 1, 2011

(87) PCT Pub. No.: WO2010/124691
PCT Pub. Date: Nov. 4, 2010

(65) Prior Publication Data
US 2012/0050058 A1    Mar. 1, 2012

(30) Foreign Application Priority Data

May 1, 2009  (DK) ................................ 2009 00568

(51) Int. Cl.
*A61G 7/018*  (2006.01)
*G06F 19/00*  (2011.01)
*A61G 7/002*  (2006.01)

(52) U.S. Cl.
CPC ........... *A61G 7/018* (2013.01); *G06F 19/327* (2013.01); *A61G 7/002* (2013.01)

(58) Field of Classification Search
CPC .. A61G 7/05; A61G 7/018; A61G 2007/0507; A61G 2007/0509; A61G 7/002; G06F 19/327; A06F 7/04
USPC ................................................ 340/5.2, 686.1
See application file for complete search history.

(56) References Cited

U.S. PATENT DOCUMENTS

| | | | |
|---|---|---|---|
| 6,539,566 B1 | 4/2003 | Hayes | |
| 8,040,082 B2 | 10/2011 | Bastholm | |
| 2005/0146431 A1* | 7/2005 | Hastings | A61B 5/002 340/539.12 |
| 2007/0105572 A1* | 5/2007 | Kim | 455/466 |
| 2007/0143920 A1* | 6/2007 | Frondorf | A61G 7/005 5/81.1 R |
| 2009/0049610 A1* | 2/2009 | Heimbrock | A61G 7/008 5/600 |
| 2010/0187379 A1 | 7/2010 | Kragh et al. | |

FOREIGN PATENT DOCUMENTS

| | | | |
|---|---|---|---|
| WO | WO01/85085 A2 * | 5/2001 | ............. A61G 7/018 |
| WO | 0185085 | 11/2001 | |

* cited by examiner

*Primary Examiner* — An T Nguyen
(74) *Attorney, Agent, or Firm* — Dykema Gossett PLLC

(57) ABSTRACT

Height adjustable beds involve the risk for the patient to fall out of the bed. In order to prevent this to happen, the bed is furnished with a device which observes whether a nursing person is within a proximity zone of the bed. When the nursing person leaves the proximity zone and the bed is adjusted to a height implying potential danger for the person in the bed, a message (sms) is sent to a mobile unit carried by the nursing person. The indication warns the nursing person, making it possible for him to prevent the potential dangerous situation by height adjustment of the bed to a safe height for leaving the bed. Hereby personal injury is prevented or minimized as much as possible.

14 Claims, 2 Drawing Sheets

BED

BACKGROUND OF THE INVENTION

Field of the Invention

The invention relates to a bed.

The Prior Art

Hospital beds and care beds are typically height adjustable, likewise the support frame is adjustable to a given shape with its backrest and legrest raised. An example of such a bed is known from, e.g., WO 00/33785 to Huntleigh Technology plc, on which the sub frame comprises a scissor mechanism. Also height adjustable beds based on columns with telescopic members are known. A column for a height adjustable bed is known from, e.g., WO 2009/033486 to Linak A/S.

The purpose of adjusting the shape of the support frame is to create better comfort for the patient, or to support a part of the body. The height adjustment is carried out to create a better working position for the nursing staff in relation to the working area of the patient. When carrying out the work the bed is adjusted with the support frame raised. Having finished the working task, the height of the bed should be adjusted to a level at which the patient can leave the bed himself. Unfortunately, it happens that the nursing staff forgets to readjust the bed to the low level which increases the risk that the patient falls when he leaves the bed. The damage connected to the fall is often extensive and results in worsening of the general condition of the patient. The same kind of problems arise when the patient, by faulty operation of the adjusting mechanisms of the bed, adjusts the height of the bed.

The purpose of the invention is to provide a solution securing an adjustable bed, which in connection with the nursing of the patient has been height adjusted, is readjusted to a height position, making it safe for the patient to leave the bed. At the same time a solution is required which prevents the patient from operating the parts of the adjusting mechanism which can be dangerous for the patient.

SUMMARY OF THE INVENTION

According to the invention this can be achieved by a bed having a control for registering the proximity of an authorized person, so that it is possible to prevent the bed from being wrongly height adjusted, and the support frame hereby is raised to a level that high that the patient can be damaged when leaving the bed. The control will therefore only allow height adjustment of the support frame when a person authorized to adjust the height of the bed, e.g., a nursing person is close to the bed.

In that the control is furnished with means to determine whether the support frame is raised to a level relative to a safe height for leaving the bed, the control can determine whether it is a question of a potential dangerous situation with the support frame of the bed raised, and the nursing staff being absent.

The presence of a nursing person can be registered by furnishing the control with a receiver for receiving a signal from a mobile unit carried by the nursing staff.

When a signal is received, the control determines whether it is a signal sent from an approved mobile unit after which the control interconnects the receiver and the sender as an interacting electronically locking mechanism allowing control of the bed for height adjustment of the bed.

Furthermore, the control is furnished with means to determine whether the nursing person again is moving away from the bed in that the connection between the two units functioning as interacting electronically locking mechanisms is broken. If then the support frame of the bed is raised and the responsible nursing person is outside normal working range in which the connection between the two units is maintained, the control is adapted to indicate that a potential risk of the patient falling out of bed is present.

The indication can be presented in the form of an acoustic or a visual signal given from a signal system in the bed. In another embodiment the signal system is placed in a position where the nursing staff can see it clearly. In an embodiment the signal is forwarded to a central watch system from which a signal can be sent to a mobile receiver carried by the nursing staff, in order to give assistance in order to prevent the problem.

The mobile unit carried by the nursing staff is particularly suitable in that it is both a sender and a receiver. The other part of the interacting electronically locking mechanism, arranged in connection with the control, is also both a sender and a receiver, a connection between the control and the mobile unit can therefore be sent from the control unit directly to the mobile unit and can be received by the mobile unit. First and foremost is thought of that an indication of the bed being height adjusted to a potential dangerous height level can reach the nursing person when he is outside the range in which the connection between the two units is maintained. That the connection is broken indicates that the strength of the signal for communication between the two units has reached a certain low level. The threshold of the signal level of the connection between the two units does not necessarily mean that the communication between the two units is disconnected, but only serves to describe the spreading of the proximity zone.

A mobile unit suitable to be carried by a nursing person could be a mobile phone where the messenger (sms) function is used to send an indication of the dangerous situation from the unit attached to the control. The connection between the unit of the bed and the mobile unit is performed via Bluetooth whereby the two units either actively or automatically are interconnected when they are within a carefully metered range of each other. When the distance between the receiver in the control and the mobile unit is increased, the connection between the units is broken when a nursing person is moving outside their range. When the support frame of the bed is adjusted to a height which could lead to a potential dangerous situation for the user, the information is connected with the information about the absence of the nursing person, and is indicated as a potential risk. When the control is furnished with a list connecting the unique Bluetooth identification of the mobile unit with the phone number of the mobile unit, it is possible in a simple way to send an indication of the dangerous situation to the receiver in the form of a message (sms).

In an embodiment the mobile unit is adapted such that it indicates by itself when a connection is broken. In this way the nursing person is urged to consider whether the bed has been adjusted back to the low level. This function could very well be combined with a parallel function of the bed, whereby a message (sms) is sent to warn the nursing person about the bed being left in a height adjustment being potential dangerous. When the mobile unit has means to receive status messages from the bed via Bluetooth, the mobile unit can use the latest status from the bed before the connection between the two units is broken to determine whether the bed is adjusted to a height which is potential dangerous for the patient. In this case an indication can be given.

Besides, the connection between the two interacting electronically locking mechanisms is performed in a similar manner as between a mobile phone and a wireless headset or a carkit. When the phone is inside the working range of the equipment in question, a connection is established. Similarly, the connection between for example a RFID and a receiver adapted for the purpose could be established. ZigBee® (ZigBee Alliance Corp.) can also be used for the purpose.

Other electromechanically resonance circuits can also be used to establish an electronic connection between interacting electronically locking mechanisms. The connection could also be established with units functioning via ultrasound, infrared light or the like. It will be appreciated that the invention comprises the basic principle that a proximity between two units will be picked up, and will establish a connection which again when the connection is broken will effect a safety operation, checking whether the bed is adjusted to a height or in a way which do not imply potential danger for the safety of the patient.

BRIEF DESCRIPTION OF THE DRAWINGS

One embodiment of the invention will in the following be explained more detailed referring to the accompanying drawings, wherein FIG. 1 schematically shows a height-adjustable hospital bed.

DETAILED DESCRIPTION OF THE DEPICTED EMBODIMENT

Figure 1:
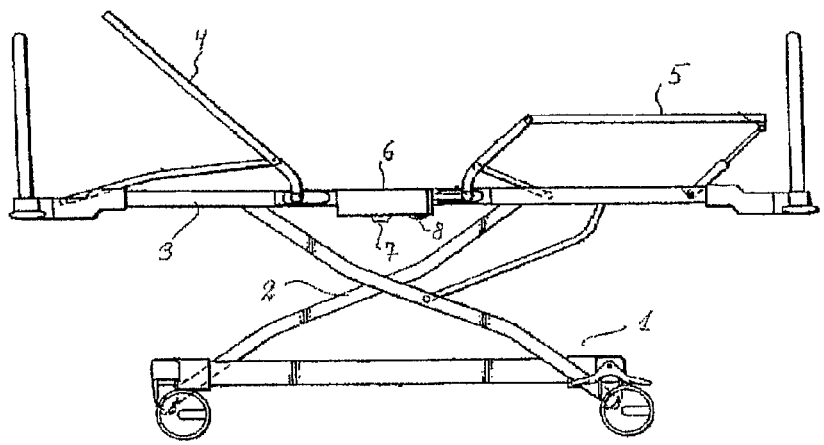

The hospital bed shown in the drawing comprises a height adjustable sub frame 1 furnished with drive wheels. The height adjustment is carried out with a scissor mechanism 2 upon which a support frame 3 for a mattress is mounted. The support frame is furnished with a height adjustable backrest 4 and legrest 5. Adjustments are made with linear actuators mounted in a fixed middle section 6, and in which a power supply and a control 7 are also mounted. In connection with the control a unit for wireless communication is arranged including a wireless communication with short range (SR) and a parallel wireless communication with long range (LR). The bed can be adjusted by a hand operator and/or fixed operating panels as known.

Furthermore, the control is furnished with means to determine to which height the support frame is adjusted. This height is proportional with the displacement of the movable activating element of the actuator. The activating element is fastened to the spindle nut. The spindle nut is moving lengthwise direction of the spindle when the spindle nut is locked against rotation, and the spindle at the same time is rotated in one or the other direction. The position of the spindle nut on its migration on the spindle can be determined with an absolute position determination system, e.g., a potentiometer. An incremental position determination system, counting the number of revolutions of the spindle and from the pitch of the spindle can generate the displacement of the spindle nut on the spindle, can also be used. An example of that is given in WO2007131509 to Linak A/S, which is hereby by reference made a part of the application.

The control is hereby furnished with the necessary input for determining the height adjustment of the support frame. When the height exceeds a fixed threshold value, as defined in the control for being a safe height for leaving the bed, the control enters into a mode in which it is testing whether a nursing person is near.

Figure 2:
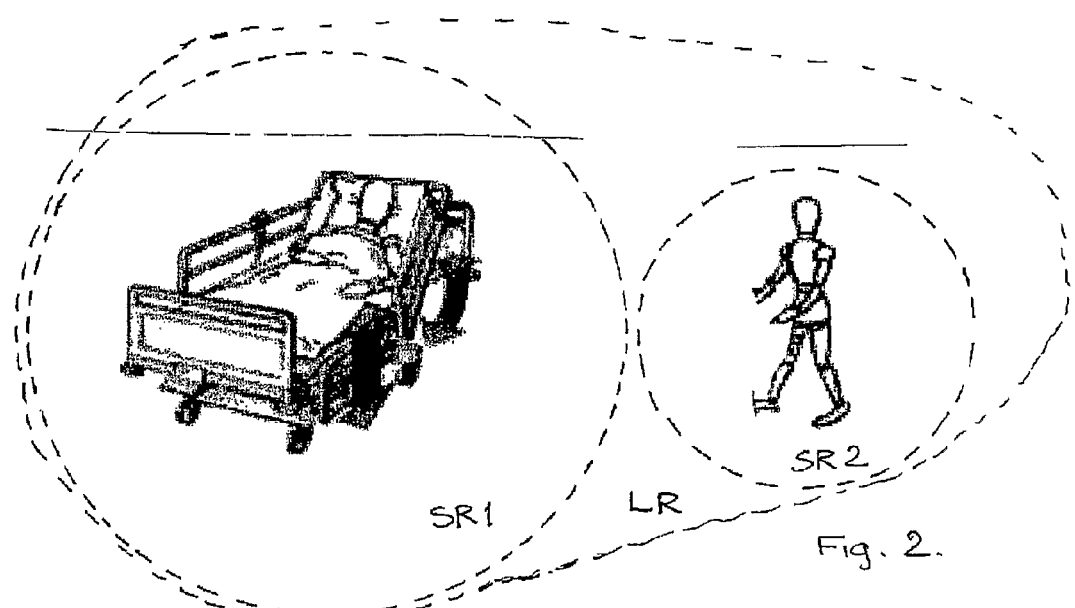
FIG. 2 illustrates a proximity zone between a bed and a nursing person.

As shown in FIG. 2, the control includes a unit having means to communicate with a mobile unit carried by the nursing person. The communication unit is created to proceed via Bluetooth (SR) and GSM (LR). Thus, the communication unit in the control and the mobile unit are as a first priority adapted to connect the two units (SR) when these are within a proximity zone of each other. The proximity zone in question has a very short working range which means that the connection again is broken when the nursing person is moving outside a certain range from the bed. When the connection between the two units is established, exclusive control units, reserved the nursing staff, but none the less put on the operating panel, are unlocked for use and can be operated by the nursing staff. When the mobile unit is moving outside the proximity zone, it becomes impossible to adjust the bed. At the same time it is tested whether the support frame is raised to a potential dangerous height for leaving the bed. Is this the case an indication about the dangerous situation is sent to the nursing staff as a sms via the GSM-net. Of course, other mobile communication systems, e.g., UMTS can also be used for this purpose, to send an indication about the dangerous situation to a nursing person, therefore it will be appreciated whether the function to send an indication about the dangerous situation, as such, irrespective of the communication means, is comprised by the application.

Figure 3:
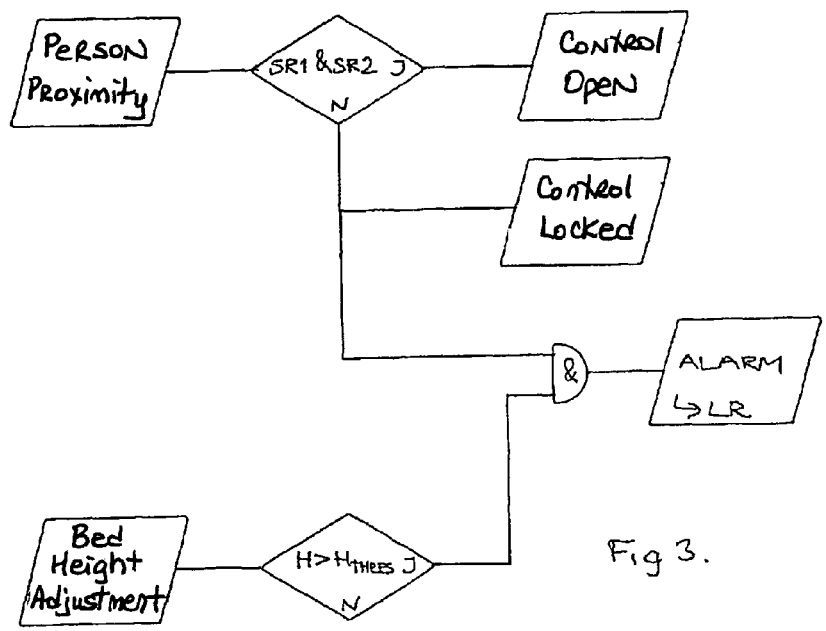
FIG. 3 shows a flow diagram for executing a safety test.
Figure 4:
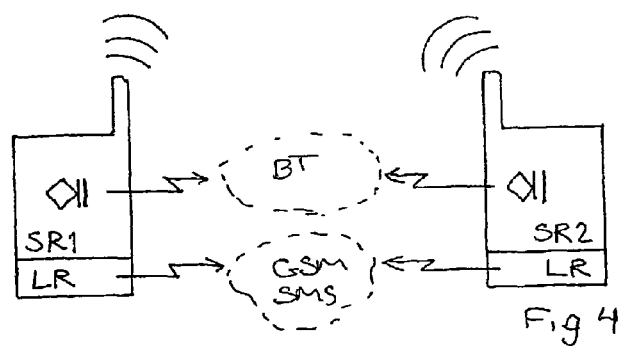
FIG. 4 illustrates communication to a nursing person about a potential danger for the safety of the patient.

FIG. 3 shows a flow diagram which in the control is converted to program code for execution of the application in a microprocessor. As it appears an indication is released when the support frame of the bed is adjusted to a height being potential dangerous when the patient is leaving the bed, and the nursing person is absent. FIG. 4 shows the two units with SR and LR communication means built in. The function is as described to send a message (sms) when the bed is height adjusted, and the proximity zone between the two units is broken to indicate that a dangerous situation has occurred.

According to the invention there is thus provided a bed with a high degree of safety against a person falling out of a height adjustable bed. An indication whether a nursing person is present together with a measurement indicating whether the support frame of the bed is in a potential dangerous height position, and an indication in the form of a message (sms) secures that the nursing person will observe the danger, and can prevent the situation. At the same time the invention secures that the height adjustment of the support frame of the bed can only be activated when a nursing person is present. Hereby is avoided that the patient by faulty operation of the operating panel causes a situation whereby the bed is potential dangerous to leave.

In spite of the fact that the focus here is on height adjustment of the bed and the dangers which can occur in this connection, the invention also includes other scenarios in connection with an adjustable bed of which an exclusive operation possibility for a present nursing person, in relation to the functions being at the disposal for the patient, is required.

Signing off the alarm situation happens automatically when the nursing person's mobile communication unit again is connected to the communication unit which is connected to the control. When the alarm is not signed off within a fixed period of time yet another message (sms) can be sent from the communication unit which is connected with the control. An additional safety measurement is created in that a message (sms) can be sent to an alternative receiver if the dangerous situation is not relieved within a fixed period of time. Hereby another possibility of relieving the dangerous situation is achieved, and hereby improved safety for the patient.

The invention claimed is:

1. A bed comprising:
a height adjustable sub frame including wheels configured to rest on the ground,
an adjustable support frame for a mattress mounted on the sub frame, said adjustable support frame including an adjustable backrest and an adjustable leg rest, said support frame being adjustable in height relative to said sub frame
a plurality of actuators for height adjustment of the support frame, said adjustment of the backrest and the legrest,
a control for the plurality of actuators,
an operating device to operate the plurality of actuators via the control wherein the operating device includes a height adjustment control unit for controlling the height adjustment of the support frame, and
wherein the control includes
means to register a person authorized to carry out height adjustment of the sub frame and thereby the support frame of the bed when the person is proximate to the bed,
means to determine a support frame height level to which the support frame has been adjusted wherein the support frame height level defines a user egress height;
means to determine whether the determined support frame height level is above a certain level, said certain level indicating a maximum height of the support frame above the sub frame corresponding to the maximum height of the support frame above the ground on which the wheels rest for safely leaving the bed and thereby prevent a user from injury when actually leaving the bed,
wherein said determined support frame height level is proportional with a displacement of a movable activating element of one of the plurality of actuators, wherein the activating element comprises a spindle and wherein the means to determine the support frame height level comprises an absolute position determination system configured to determine a position of a spindle nut that moves in a lengthwise direction of the spindle when the spindle is rotated, wherein the absolute position determination system comprises a potentiometer,
a receiver for receiving a signal from a sender in the form of a mobile unit carried by a person who is authorized to carry out height adjustment of the bed, and
wherein the control interconnects the receiver and the sender as an interacting electronically locking mechanism, the control deactivates to lock and prevent from use the height adjustment control unit of the operating device when the receiver and the sender are not in a common proximity zone, the control unit further unlocking the height adjustment control unit of the operating device of the bed when both receiver and sender are in a common proximity zone.

2. The bed according to claim 1, wherein the control tests whether the bed is height adjusted above a certain level indicated as a safe height for leaving the bed, and if above a safe height, the control indicates the dangerous situation when the connection is disconnected between the mobile unit and the receiver, functioning as interacting electronically locking mechanisms.

3. The bed according to claim 2, wherein the control indicates the dangerous situation acoustically, optically or electronically, and wherein an electronic indication in the form of a message (sms) is sent.

4. The bed according to claim 1, wherein interconnection between the mobile unit and the receiver occurs via Bluetooth and communication via GSM as text messages.

5. The bed according to claim 1, wherein the mobile unit carried by the authorized person is adapted to collect data from the control itself via Bluetooth about the state of the height adjustment of the bed, and when connection between the mobile unit and the receiver indicating the proximity zone is broken, controls the state of the bed, and afterwards if the bed is height adjusted to a dangerous level for leaving the bed, the control sends a warning signal to the mobile unit.

6. The bed according to claim 1, wherein the control is configured to provide an indication of a dangerous situation in the form of an acoustic or a visual signal placed in a position where nursing staff can receive said acoustic or visual signal.

7. The bed according to claim 1, wherein the control is configured to provide an indication of a dangerous situation in the form of a signal that is forwarded to a central watch system from which a further signal can be sent to a further mobile receiver carried by nursing staff.

8. A bed comprising:
a height adjustable sub frame including wheels configured to rest on the ground,
an adjustable support frame for a mattress mounted on the sub frame, said adjustable support frame including an adjustable backrest and an adjustable leg rest, said support frame being adjustable in height relative to said sub frame
a plurality of actuators for height adjustment of the support frame, said adjustment of the backrest and the legrest,
a control for the plurality of actuators,
an operating device to operate the plurality of actuators via the control wherein the operating device includes a height adjustment control unit for controlling the height adjustment of the support frame, and
wherein the control includes
means to register a person authorized to carry out height adjustment of the sub frame and thereby the support frame of the bed when the person is proximate to the bed,
means to determine a support frame height level to which the support frame has been adjusted wherein the support frame height level defines a user egress height;
means to determine whether the determined support frame height level is above a certain level, said certain level indicating a maximum height of the support frame above the sub frame corresponding to the maximum height of the support frame above the ground on which the wheels rest for safely leaving the bed and thereby prevent a user from injury when actually leaving the bed, wherein said determined support frame height level is proportional with a displacement of a movable activating element of one of the plurality of actuators, wherein the activating element comprises a spindle and wherein the means to determine the support frame height level comprises an incremental position determination system configured to count a number of revolutions of the spindle and from a pitch of the spindle generate a displacement of a spindle nut that moves in a lengthwise direction of the spindle when the spindle is rotated, a receiver for receiving a signal from a sender in the form of a mobile unit carried by a person who is authorized to carry out height adjustment of the bed, and wherein the control interconnects the receiver and the sender as an interacting electronically locking mechanism, the control deactivates to lock and prevent from use the height adjustment control unit of the operating device when the receiver and the sender are not in a common proximity zone, the control unit further unlocking the height adjustment control unit of the operating device of the bed when both receiver and sender are in a common proximity zone.

9. The bed according to claim 8, wherein the control tests whether the bed is height adjusted above a certain level indicated as a safe height for leaving the bed, and if above a safe height, the control indicates the dangerous situation when the connection is disconnected between the mobile unit and the receiver, functioning as interacting electronically locking mechanisms.

10. The bed according to claim 9, wherein the control indicates the dangerous situation acoustically, optically or electronically, and wherein an electronic indication in the form of a message (sms) is sent.

11. The bed according to claim 8, wherein interconnection between the mobile unit and the receiver occurs via Bluetooth and communication via GSM as text messages.

12. The bed according to claim 8, wherein the mobile unit carried by the authorized person is adapted to collect data from the control itself via Bluetooth about the state of the height adjustment of the bed, and when connection between the mobile unit and the receiver indicating the proximity zone is broken, controls the state of the bed, and afterwards if the bed is height adjusted to a dangerous level for leaving the bed, the control sends a warning signal to the mobile unit.

13. The bed according to claim 8, wherein the control is configured to provide an indication of a dangerous situation in the form of an acoustic or a visual signal placed in a position where nursing staff can receive said acoustic or visual signal.

14. The bed according to claim 8, wherein the control is configured to provide an indication of a dangerous situation in the form of a signal that is forwarded to a central watch system from which a further signal can be sent to a further mobile receiver carried by nursing staff.

* * * * *